United States Patent [19]
Friese et al.

[11] Patent Number: 5,545,301
[45] Date of Patent: Aug. 13, 1996

[54] SENSOR ELEMENT FOR THE DETERMINATION OF CONCENTRATION OF GAS CONSTITUENT(S)

[75] Inventors: Karl-Hermann Friese, Leonberg; Werner Gruenwald, Gerlingen; Roland Stahl, Freiberg a. Neckar; Claudio de la Prieta, Stuttgart; Gerhard Schneider, Vaihingen/Enz; Harald Neumann, Vaihingen/Enzweihingen, all of Germany

[73] Assignee: Robert Bosch GmbH, Stuttgart, Germany

[21] Appl. No.: 360,737

[22] Filed: Dec. 23, 1994

[30] Foreign Application Priority Data

Apr. 23, 1993 [DE] Germany ............... 43 13 251.0

[51] Int. Cl.$^6$ ............................................. G01N 27/26
[52] U.S. Cl. .................... 204/425; 204/427; 204/424; 204/431; 204/432
[58] Field of Search ..................... 204/431, 432, 204/425, 427, 424

[56] References Cited

U.S. PATENT DOCUMENTS

| | | | |
|---|---|---|---|
| 4,450,065 | 5/1984 | Yamada et al. | 204/412 |
| 4,657,659 | 4/1987 | Mase et al. | 204/410 |
| 5,106,482 | 4/1992 | Milstein et al. | 204/432 |
| 5,174,885 | 12/1992 | Hayakawa et al. | 204/427 |

FOREIGN PATENT DOCUMENTS

| | | |
|---|---|---|
| 0123720 | 11/1984 | European Pat. Off. |
| 0144057 | 6/1985 | European Pat. Off. |
| 0188900 | 7/1986 | European Pat. Off. |
| 0516038 | 12/1992 | European Pat. Off. |
| 3728289 | 8/1988 | Germany |
| 3910272 | 10/1989 | Germany |
| 91/14174 | 9/1991 | WIPO |

OTHER PUBLICATIONS

Zhang et al: "Prediction of the Effective Diffusivity in Pore Networks Close to a Percolation Threshold." AIChE Journal, Nov. 1992, vol. 38, No. 11, pp. 1816–1824.

Primary Examiner—Bruce F. Bell
Attorney, Agent, or Firm—Spencer & Frank

[57] ABSTRACT

A sensor element for determining concentration of at least one constituent of a gas mixture operates on an electrochemical measuring process and includes a gas measuring chamber; a pair of electrodes and an electrode chamber located between the pair of electrodes; and a diffusion conduit adjoining the electrode chamber and having a gas input which connects with the gas measuring chamber, having a gas output which connects with the electrode chamber, and having at least one cross-sectional area including a height, w, and a length, L, which height, w, has a preselected minimum value, and which length, L, has a value which is equal to or greater than the preselected minimum value of the height, w. The constituent of the gas mixture has a mean free path length through the sensor element, the gas measuring chamber has a cross-sectional area including a height and a length each of which are at least as large as the minimum height, w, of the diffusion conduit, and the height, w, of respective ones of the at least one cross-sectional area of the diffusion conduit is at least a multiple of the mean free path length of the constituent of the gas mixture to be measured. Advantageously, substantially only gaseous phase diffusion occurs when the predetermined minimum value of the height, w, is at least a multiple of a minimum value of the mean free path length for the gas constituent measured.

16 Claims, 8 Drawing Sheets

SENSOR ELEMENT FOR THE DETERMINATION OF CONCENTRATION OF GAS CONSTITUENT(S)

BACKGROUND OF THE INVENTION

1. Field of the Invention

The invention relates to a sensor with a diffusion conduit, for example, for measuring the exhaust gas of internal combustion engines, in accordance with the species of the main claim, in various embodiments, mostly as laminar or finger probes, which are embodied with various hollow chamber systems, i.e., measuring chambers.

2. Description of the Related Art

A sensor of the species is known from EP-A 0 188 900, wherein the design of the gas measuring chamber with its diffusion conduit is fixed by the relationship between distances which were empirically determined for different designs. This relationship was constant, independently of the design of the probe which was embodied flat, and determined the distances of the exhaust gas chamber in relation to the electrodes and their geometry.

The mathematical relationship m−1>5 w, or in the borderline case m−1=5 w in EP-A 0 188 900, wherein 1 is the distance between the inlet of the gas measuring chamber and a next closest point of the first electrode in relation to the inlet, m is the distance between the inlet of the gas measuring chamber and a next closest point of the third electrode in relation to the inlet, and w the distance between the first and third electrodes exposed to the exhaust gas, relates to a planar arrangement which was laminarly constructed.

This formula loses its applicability in case of dimensions corresponding to atomic orders of magnitude, and in connection with very small dimensions would lead to the liquefaction of the gas because of wall reactions and adsorptions (Lin Zhang and Nigel A. Seaton, Prediction of the Effective Diffusity in Pore Networks Close to the Percolation Threshold, AIChE Journal 38, 1992, 1816–1824). Furthermore, because of the planar electrode arrangements, a measurement can mostly be performed only with homogeneous electrical fields.

A further limitation for gas flows from the gas measuring chamber in the disk-shaped diffusion conduit is the result of the right-angled deflection of diffused gas components, even in the case where w already assumes the multiple size of the diameter of the gas component.

Such a sensor element is constructed from a base body of, for example, zirconium dioxide ceramic material, which is used as a solid body electrolyte. For reasons of economics, a laminar construction of the sensor is advantageous, however, this is not the only design.

Examples of exhaust gas probes as EGOS (exhaust gas oxygen sensor), HEGOS (heated EGOS), PEGOS (proportional EGOS), UEGOS (universal EGOS) and TF-HEGOS (thin film HEGOS). Measurements are performed in the electro-chemical sensor element, among others in a marginal current probe, with at least two electrodes, one of which can come into contact with the reference gas, the other with the exhaust gas.

The gas component to be measured comes into complete contact with the porous electrode. This can lead to contamination or overloading of the contact surface in case of the appearance of saturation effects on the electrode surface because of the complete coverage with one or several gas components.

Sensors of this type operate in accordance with polarographic measuring principles. In the process, a constant electrode voltage is applied between an anode and a cathode and a diffused marginal flow is measured. However, the sensor could also operate in accordance with another electro-chemical measuring principle, for example, the potentiometric measuring principle.

The diffused marginal flow, for example in connection with a marginal flow probe, is defined by ions after they have overcome a diffusion barrier of the component of the gas to be measured, whose charges cause the current. The design of the gas measuring chamber, in particular the diffusion conduit ahead of the electrodes, determines the diffusion resistance of the measured gas and affects the gradient of the concentration of the measured gas component to be measured. A feedback to the control position of the sensor occurs.

Hereinafter, the term gas measuring chamber will also include the diffusion conduit and the electrode chamber, unless they are specifically mentioned. In a diffusion conduit which is a part of the gas measuring chamber of, for example, an exhaust gas probe, the gas mixture to be measured flows into the probe via the gas measuring chamber, which is fed from the outside. The gas measuring chamber should contain every gas chamber which can accommodate the gas component to be measured of the sensor.

The electrode chamber is the chamber located between the electrodes and containing the gas. It adjoins the diffusion conduit and at least the gas component to be measured flows through it.

Up to now, information and realizations which would permit the design of a gas measuring chamber for an exhaust gas probe which differs from a planar structure are greatly lacking. A disadvantage of the known sensors having a diffusion conduit tunnel is that the emission of signals remains sensitive to temperature and pressure or at least does not operate without interfering conditions.

A so-called mixed diffusion of Knudsen and gaseous phase diffusion exists in conventional embodiments with small dimensions of the diffusion conduit tunnel or with filled tunnels of the diffusion conduit, which could be the reason for the pressure dependency of the probe signals.

From DE-PS 37 28 289 it is known to embody diffusion conduits either with filler material for the Knudsen diffusion or without filler material for the gaseous phase diffusion and to design series and/or parallel circuits with the filler materials, which requires several production steps and results in spreading of the physical and chemical properties of the sensor specimen.

SUMMARY OF THE INVENTION

Sensor elements with diffusion conduits designed in accordance with the invention have sufficient path lengths for the measured gas components. Gaseous phase diffusion essentially occurs in this way without impacts on the wall or chemical reactions occurring which could falsify this. In this case the coefficient of diffusion of the measured gas component is reversely proportional to the pressure in the gas measuring chamber. Flow problems and tendencies for wall reactions of the gas component to be measured because of collisions of the molecules are prevented to a large extent.

Converted for a working temperature $T_2$ of 800 degrees Celsius and $p_2=1$ bar, a mean free path length of approximately 0.3 micrometers results. From this, the minimum dimensions of the diffusion conduit is determined to be 30 micrometers, which corresponds to one hundred times the mean free path length of the oxygen anion.

For functional reasons a probe is limited in its interior conduit system in respect to the volume of its gas measuring chamber and the diffusion conduit. The minimum extent of the gas measuring chamber at each location in the interior chamber of the sensor is known.

Consideration of the minimal dimension of the diffusion conduit and the gas measuring chamber provides further advantages because of its increased freedom to choose the electrode geometry, for example, in the electrode chamber. Additional components, for example, support elements of conduit expansion systems for the electrode chamber can be disposed at a suitable location.

BRIEF DESCRIPTION OF THE DRAWINGS

Advantageous embodiments of the diffusion conduit are represented in the drawings in which.

DESCRIPTION OF THE PREFERRED EMBODIMENTS

EXAMPLE 1

Figure 1:
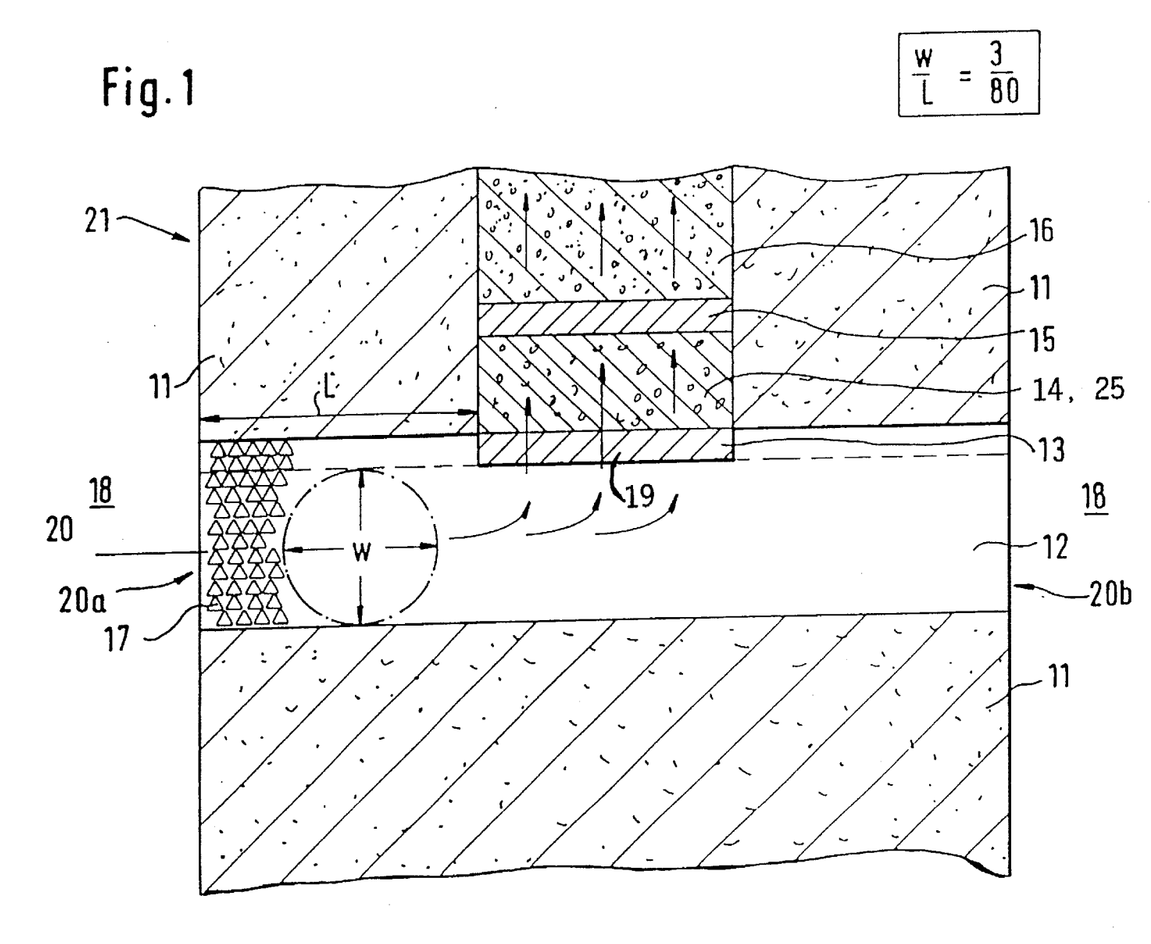
FIG. 1 shows a cross section through a gas measuring chamber having a diffusion conduit for a sensor.

A diffusion conduit 12 for oxygen gas component measuring with a minimum dimension w=30 micrometers, built on a substrate 11, is provided with a pair of electrodes consisting of a porous uncoated cathode 13 and a porous anode 15 with a porous intermediate layer 14. The porous anode 15 is covered with a covering layer 16. The minimum dimensions are indicated by a drawn-in sphere with the diameter w, which can be freely displaced. The structure, with a measurement w=30 micrometers, is constructed of a zirconium dioxide ceramic material stabilized with $Y_2O_3$ for the porous covering layer 16 and the porous intermediate layer 14, and with an aluminum oxide ceramic material for the substrate layers 11. The porous electrodes 15 and 13 are made of platinum or a platinum alloy. A ratio of the height w, which includes the minimum dimensions of the conduit, and the length L was fixed as w:L=3:80. The diffusion conduit may have a height-to-length ratio of w:L=2 to 4:70 to 90, while the minimum dimensions of the mean free path length dimension of the gas component to be measured are maintained.

In case of a larger size of w>30 micrometers, a filler material 17, for example porous $Al_2O_3$, can be introduced into the diffusion conduit. It is conceivable that the gas 20 to be measured flows into the diffusion conduit 12 of the gas measuring chamber 18 from several sides 20a, 20b. In the direction of the third dimension the exhaust gas probe 21 can also be embodied in a non-planar shape. Based on tests with more elaborate sensors, the w:L ratio could also be kept for other sensors.

It would be possible to coat the electrodes. For example, the cathode 13 can be coated with a porous protective layer or several porous protective layers to prevent corrosion effects and contaminations of its surface, as well as wear of its material, or to avoid damage and/or impairment caused by the components of the gas 20 to be measured. A diffusion conduit bent at its ends could be embodied more advantageously in respect to fluidics.

EXAMPLE 2

Figure 2:
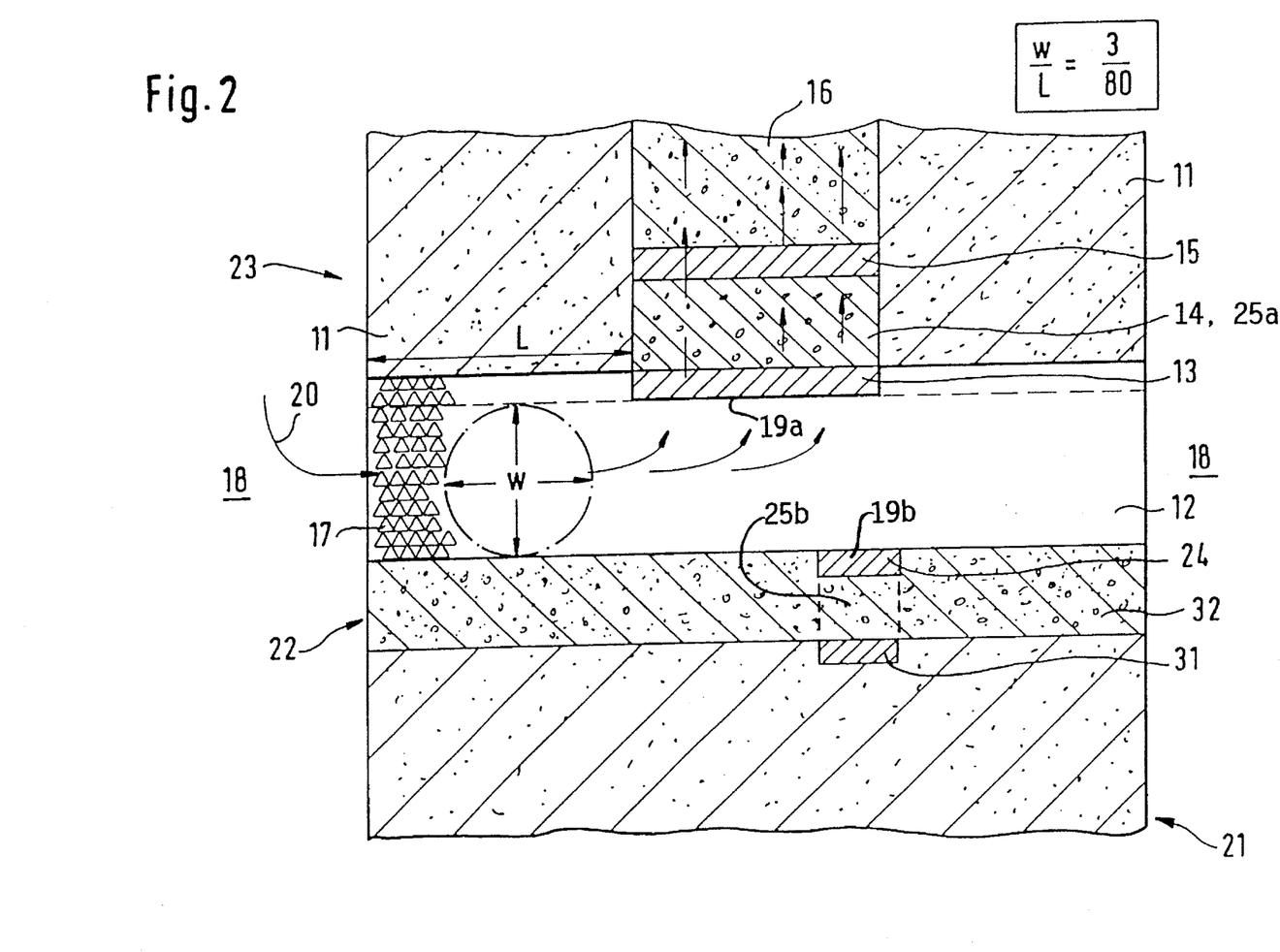
FIG. 2 shows a cross section through a sensor built from a pumping and measuring cell.

A largely pressure-independent exhaust gas probe 21, consisting of a measuring cell 22 and a pumping cell 23 is represented in FIG. 2. Not all electrodes were coated, for example the cathode 13 and the first electrode 24 are uncovered. Pumping cell includes electrode chamber 25a and measuring cell 22 includes electrode chamber 25b. Diffusion conduit 12 includes gas outlets 19a, 19b respectively to pumping cell 23 measuring cell 22.

When gas 20 to be measured enters measuring cell 22 which includes an electrode chamber to 25 defined between first and second electrodes 24, 31 via the diffusion conduit 12, it comes into contact with the first electrode 24 of the measuring cell 22, whose potential changes in respect to the second electrode 31. The first electrode 24 and the second electrode 31 are separated by an intermediate layer 32 which conducts oxygen anions. The difference in potential is detected and is used for the control of the potential between the cathode 13 and anode 15 of the pumping cell 23. The oxygen concentration to be measured is measured after the electrodes have been connected to an electric current supply net. The measuring principle is described in more detail in EP-A 0 194 082, which corresponds to U.S. Pat. No. 4,645,572, for example.

The electrodes of the measuring cell 22 can also be disposed in the center underneath the electrodes of the pumping cell 23. The number of diffusion conduits 12, their topography and their cross-sectional dimensions are decisive for their position. Furthermore, a path length for the exhaust gas is conceivable whose oxygen-gas concentration is measured at several locations in order to realize an improved control of the in flowing gas, i.e., a feed regulation for a plurality of pairs of electrodes used for measuring.

EXAMPLE 3

Figure 3:
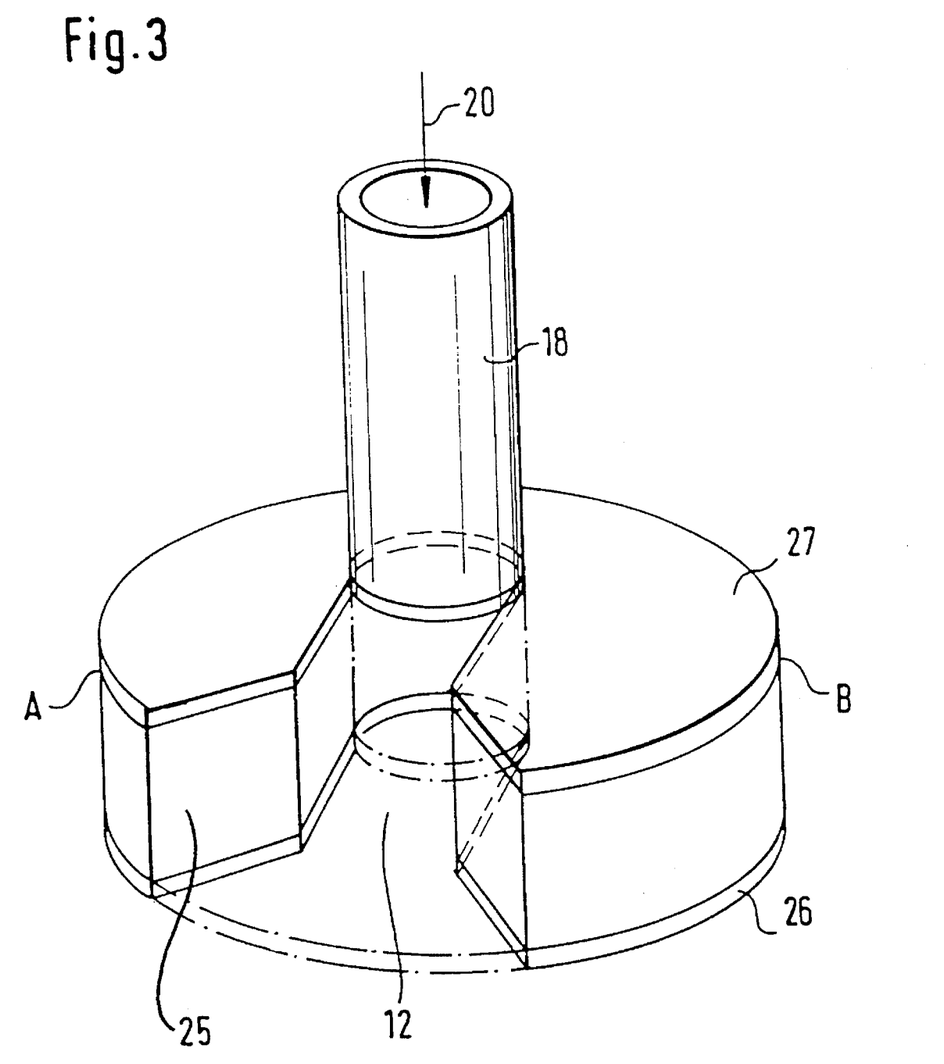
FIG. 3 shows a portion of the gas measuring chamber in cylindrical form with which a vertically disposed diffusion conduit is associated.
Figure 4:
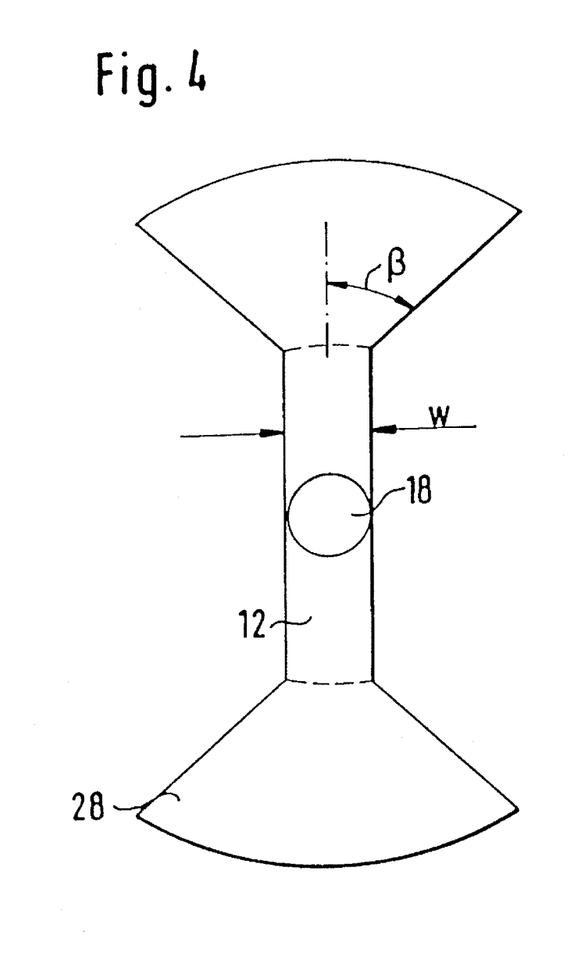
FIG. 4 shows a cross section through the gas measuring chamber of the sensor of FIG. 3 along the axis A–B with the diffusion conduit not widened.

An electrode chamber 25 is spread out in a fan shape in FIG. 3. In this electrode chamber 25 the gas 20 to be measured flows across a cylinder-shaped gas measuring chamber 18, which can also constitute a part of the volume of the gas measuring chamber, via the diffusion conduit 12. The electrode surfaces 26 and 27 in the form of a coated anode surface 26 and a coated cathode surface 27 are well suited for making contact with the electrodes. The electrodes are designed as sector-shaped sections, as shown in FIG. 4. The opening angle β is 60 degrees.

Figure 6:
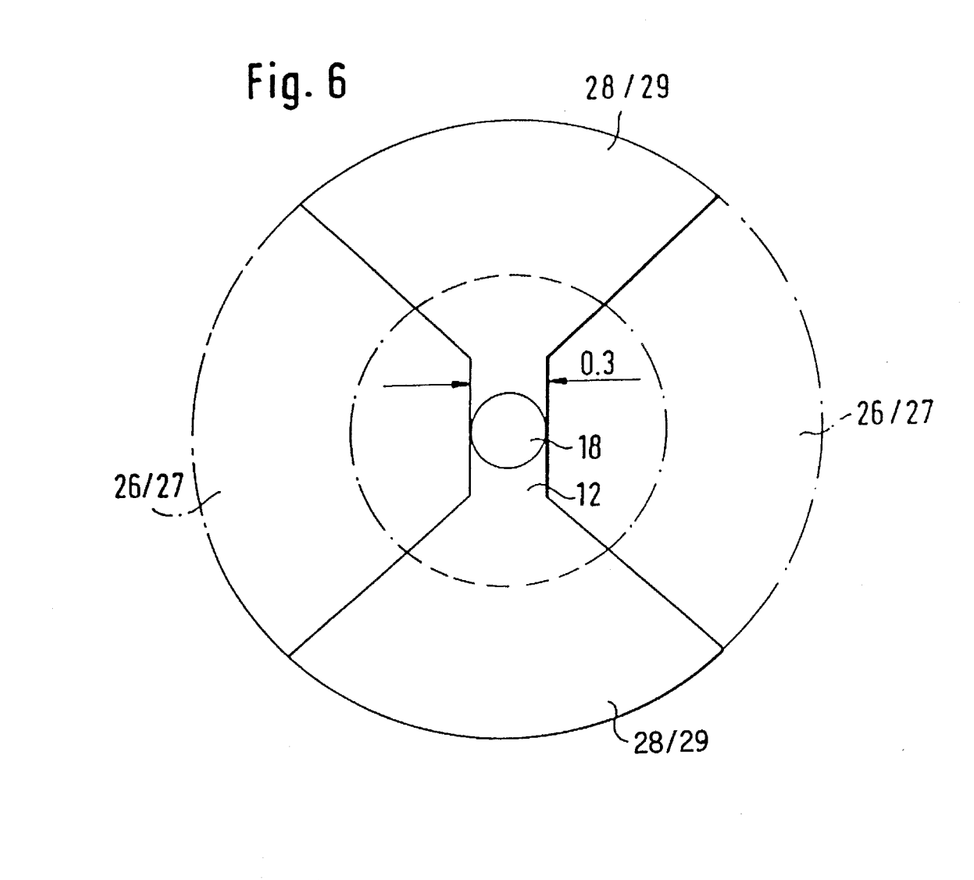
FIG. 6 shows, in the cross-hatched area, the electrode coating by means of an example of a partially coated sector of a circle, i.e., a ring electrode coating.

Because of the electrodes being contacted outside of the gas measuring chamber 18, the production options for the electrode contacts are increased. Very thin layers of different material thickness and different local composition can be realized inside the covered chamber for contacting, providing great freedom in the choice of material and thus good electrical and mechanical contacting stability and freedom from noise. The active electrode surface and a contact-providing medium for connecting the supply lines for the electrode with an exterior electrical current supply net are located in different sections, for which reason a double function at one geographical location does not force a compromise for the electrodes and the contact. As shown in FIG. 6, the covered electrode surfaces 26, 27 directly adjoin the uncovered active electrode surfaces 28, 29. It would be possible to select the opening angles for the covered and the active electrode surfaces differently on one or both sides, so that interruptions of the strip conductor are provided or are made.

A circular disk coating in an analogous variant in accordance with FIG. 6 is conceivable.

EXAMPLE 4

FIG. 4 shows a section A–B, wherein the active electrode surface 28 directly adjoins the edge of the rectangular and pillar-shaped diffusion conduit 12. The opening angle β is 45 degrees.

EXAMPLE 5

Figure 5:
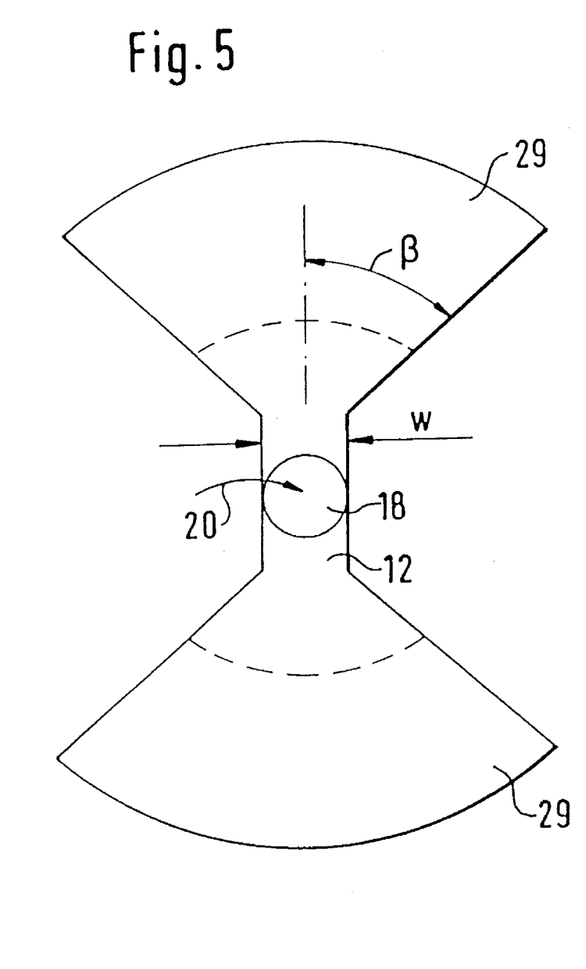
FIG. 5 shows a cross section through the gas measuring chamber of the sensor of FIG. 3 along the axis A–B with a fan-like widened diffusion conduit.

The embodiment of the exhaust gas probe in FIG. 5 and FIG. 6 is the same as in Example 3 and FIG. 3, however, the electrodes are ring-shaped. FIG. 5 shows a section A–B, wherein the active electrode surface 29 does not directly adjoin the edge of the rectangular and pillar-shaped diffusion conduit 12, but only encompasses a section of the ring. In this case the diffusion conduit 12 is also widened in a fan shape.

The opening angle β for FIG. 4 and 5 can be selected to be up to 90 degrees, depending on how many electrode chambers are connected with each other via several diffusion conduits. It would be conceivable to embody the anode surface the same as the cathode surface. Another geometry of the electrical field for measurement with non-homogeneous fields can also be produced.

EXAMPLE 6

Figure 7:
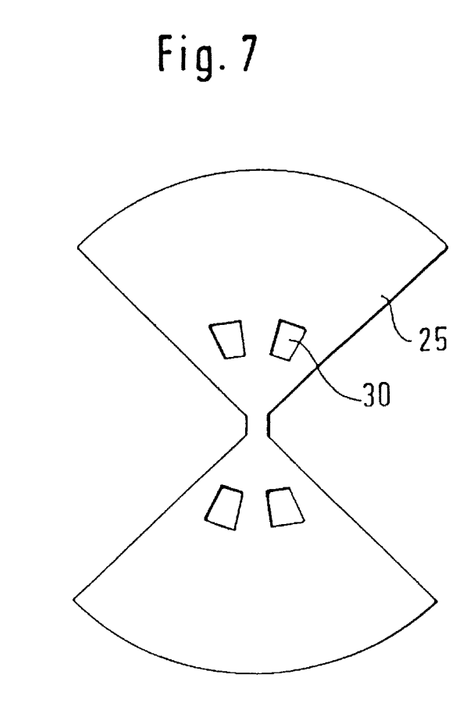
FIG. 7 shows, by means of each cross section for the angle $\beta=60$ degrees, the installation of additional structural components or structural elements (support pillars) in the electrode chamber.

An example of a cross section through the diffusion and electrode chambers of an exhaust gas probe with an inner structure is shown in FIG. 7. The column-shaped built-in pillars, i.e., hollow chamber supports 30, are used for controlling the flow of gas to be measured to the electrode surfaces. The baffle function of the columns protects the electrodes from oversaturation and contaminants. In addition, the structure becomes mechanically more stable and is easier to miniaturize.

EXAMPLE 7

It is furthermore possible to compose an exhaust gas probe of a short-circuit cell, a pumping cell and a measuring cell, as can be seen from Examples 1 and 2. The dimensions in accordance with the invention of the said examples are kept. It is also possible that a gas measuring chamber with three diffusion conduits inclined by 60 degrees in respect to each other forms a star with electrode chambers adjoining it.

It is possible to calculate the mean free path length of the gas component to be measured by means of the equation $l_2=(l_1 \cdot T_2 \cdot p_1)/(T_1 \cdot p_2)$, where the temperature $T_1$ is known, the pressures $p_1$ and $p_2$ are known and the mean free path length $l_1$ at the known temperature $T_1$ is known (Source: K. G. Müer, Vakuumtechnische Berechnungsgrundlagen [Calculation Bases in Vacuum Technology], Verlag Chemie, Weinheim 1961, page 15, 16).

For example, for air, a gas mixture of essentially $O_2$, $N_2$, $CO_2$ and noble gases, or pure oxygen $O_2$ or pure nitrogen $N_2$, this value is, at $p_1=1$ bar and 20 degrees Celsius, a mean free path length on the order of magnitude of 0.08 micrometers. With this, the minimal diameter of the diffusion conduit is calculated to be 8 micrometers at an ambient temperature of 20 degrees Celsius.

Converted to a working temperature $T_2$ of 800 degrees Celsius and $p_2=1$ bar, a mean free path length of approximately 0.3 micrometers is the result. From this the minimum dimensions of the diffusion conduit are determined to be 30 micrometers at 800 degrees Celsius.

For a size of the diffusion conduit of 30 micrometers at an operational measured temperature in the range of the ambient temperature to 800 degrees Celsius, the oxygen content at a pressure between 0.1 to 10 bar is measured in connection with the examples.

Figure 8:
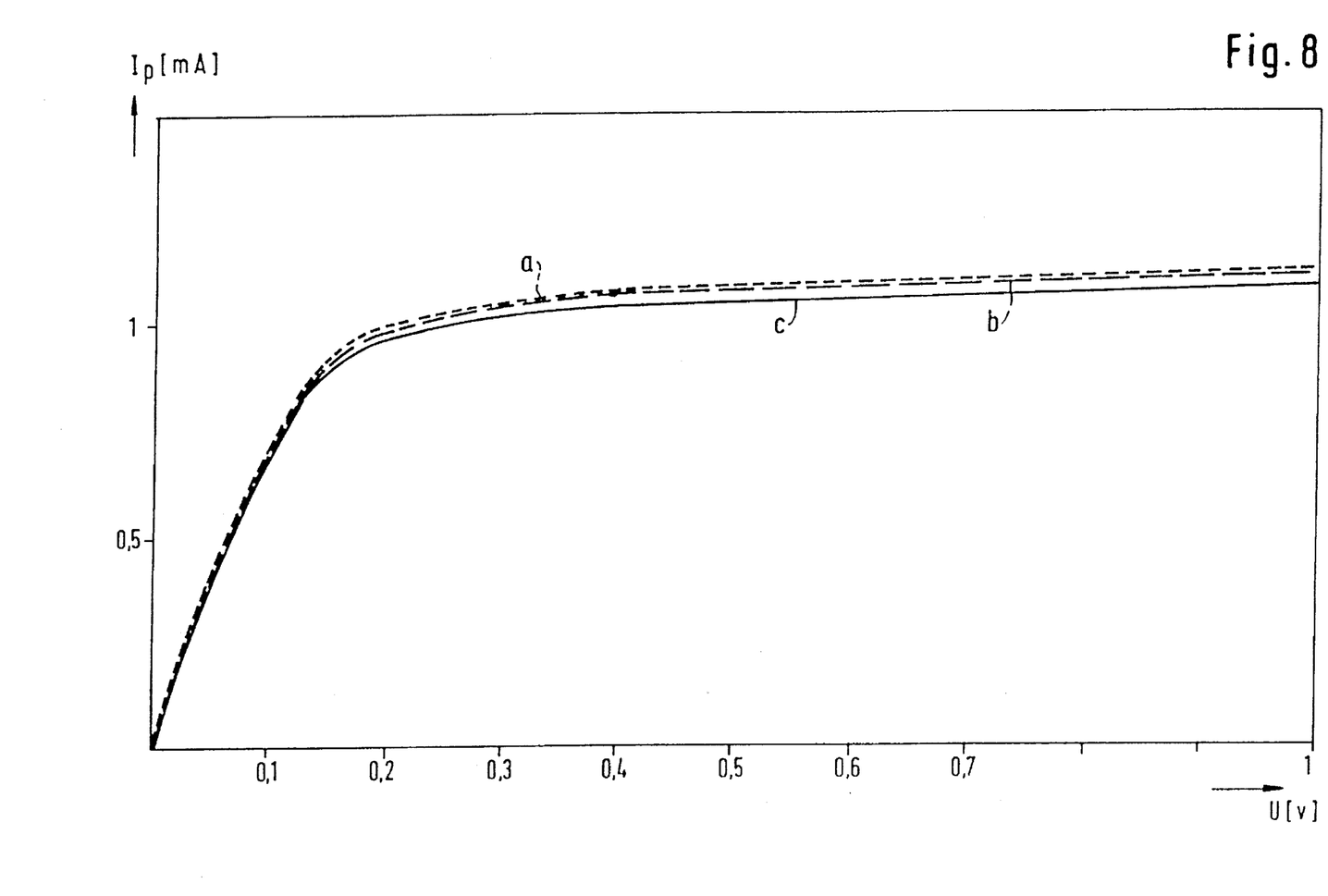
FIG. 8 shows a pumping flow-pumping voltage diagram for showing the pressure dependency of a sensor.

A measurement with two sensors of the same type, differing in the dimension w (FIGS. 1, 2), with an electrode design as in FIG. 5, was performed with w=5 and w=30 micrometers for the lateral cross-sectional dimensions of the diameter of the diffusion conduit. A marginal flow measurement for each specimen of both marginal flow sensors resulted in a pressure dependence of the measured marginal flows of 8 percent/bar at w=30 micrometers in contrast to 40 percent/bar at w=5 micrometers, as can be seen from FIG. 8 for a=1.5 bar/1.09 mA, b=1.25 bar/1.07 mA and c=1.0 bar/1.05 mA in the voltage interval.

Figure 9:
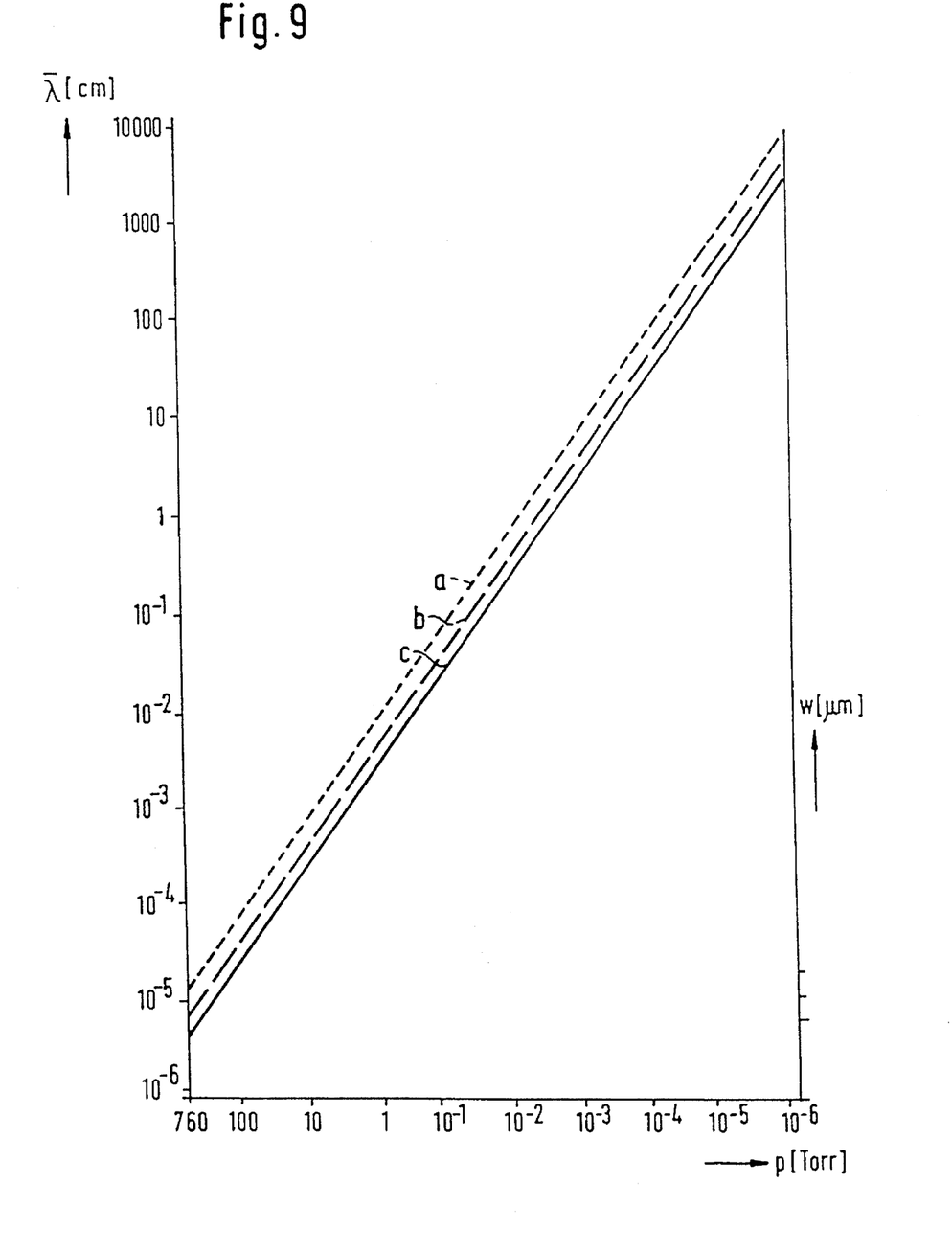
FIG. 9 shows the mean free path length for a selection of different gases as a function of the gas pressure of a gas to be measured and the conduit dimension resulting at 20 degrees Celsius.

FIG. 9 contains an example of the conduit design for the gases a $H_2$, b air, c $CO_2$ and represents on the vertical axes the mean free path length on the left and the conduit dimension w on the right. The horizontal axis represents the gas pressure. A diffusion conduit dimension of w=22 micrometers results for carbon dioxide and analogously w=80 micrometers is applicable for hydrogen.

Figure 10:
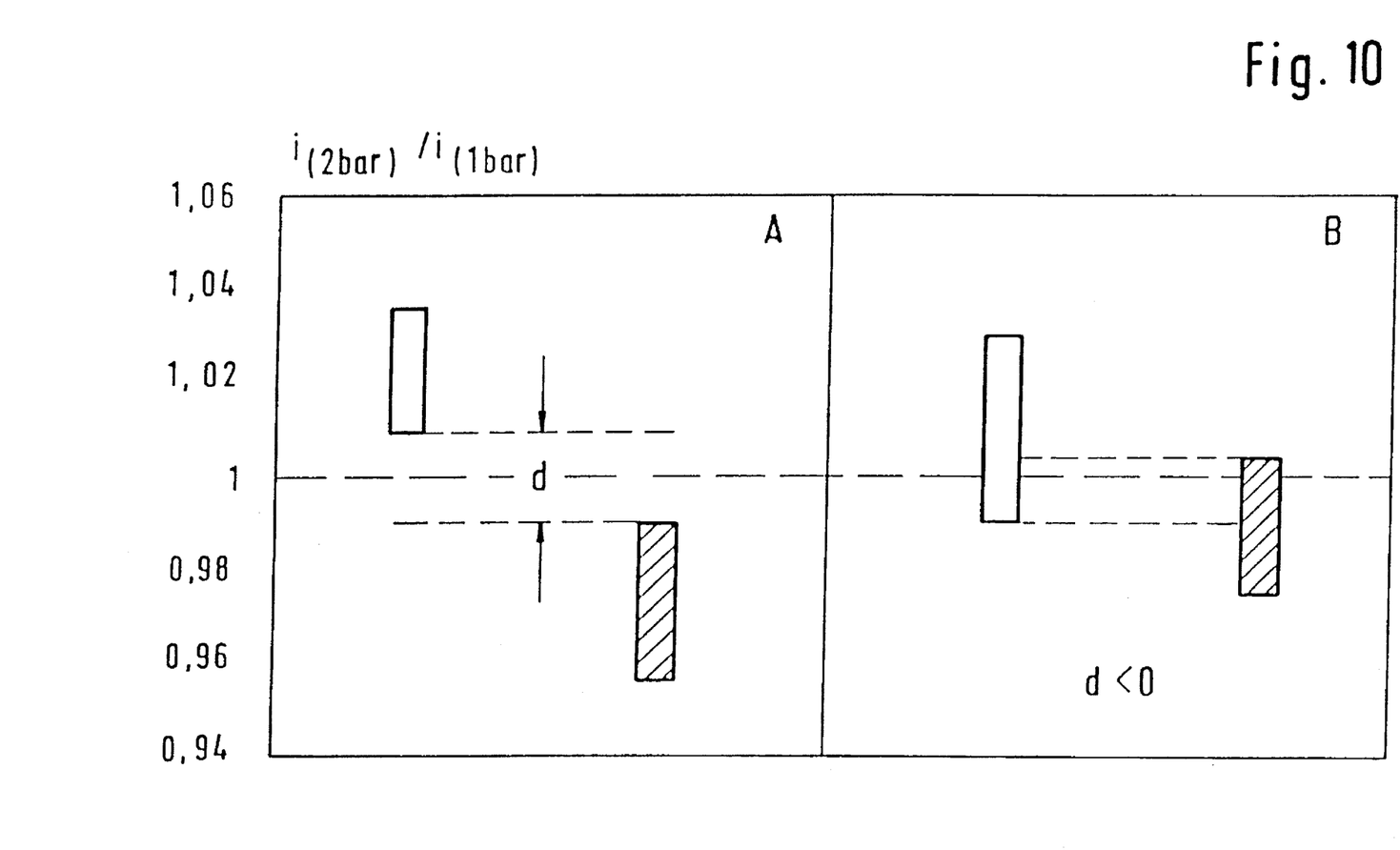
FIG. 10 shows the operation of an uncontrolled.

An example of the lack of pressure sensitivity of a probe, for example, the probe in accordance with FIG. 2, is represented in FIG. 10. The probe can be heated if a heating element is attached to the lower substrate of the exhaust gas probe. For two exhaust gas probes A and B designed in this way, with electrode chambers in accordance with FIG. 4 and FIG. 5, respectively FIG. 10 shows the relation of the marginal flows of these probes at different temperature stabilities, set by the heating output.

The respective relation of the marginal flows of two different probes whose electrode chambers correspond to those of FIG. 4 and FIG. 5 are shown in FIG. 10 at an ambient gas pressure of 1 bar or increased air pressure of 2 bar. Cross-hatched areas identify changeable temperatures of the gas, blank surfaces indicate constant temperatures. In the case of the probe of FIG. 4, the dashed lines clearly show no overlapping of the measuring fields for constant and differing temperatures and therefore a slightly greater temperature sensitivity of this layout for the exhaust gas measurement of the oxygen concentration. A marginal flow relation of i (2 bar)/i (1 bar)=1 is defined as the operating point.

The embodiment of FIG. 5 proved to be better than the embodiment shown in FIG. 4. The height of the rectangles in FIG. 10 includes the production scattering of different specimens of the probe type produced in accordance with the invention.

In FIG. 10, the best embodiment of a probe is the probe B, with small rectangular surfaces of FIG. 10, which are distributed at the same height symmetrically around the marginal flow relation, at a set value of 1 for the marginal flow relation at different pressures. The parameter d is a measure for the lack of overlapping of the operational point of the exhaust gas probes A or B). The invention generally relates to sensors in which a diffusion barrier is placed upstream of a reaction electrode.

A technique for producing an exhaust gas probe is that of screen printing of, for example a crackable organic shaping layer, the shaping means, or a part of a body of this material, on a substrate 11 or generally on another layer. Taking into consideration the amounts of shrinkage of the ceramic material used, the form and dimensions of the hollow chamber of the gas measuring chamber 18, i.e., also the w/L relation, are determined. This screen-printed layer, for example, constitutes the diffusion conduit volume. Following the laminating together of all layers of which the sensor is built, the gas measuring chamber 18 is subsequently decomposed, evaporated or burned out during sintering. The sandwiching can include, for example, adaptation, electrode, catalyst, supply, cover or ceramic layers of the exhaust gas probe and, if desired, can be mechanically performed. Frequently the ceramic layers are between 0.3 and 2 millimeters thick.

A manufacturing process of the diffusion barrier by sintering requires a minimum height of the conduit of 30 micrometers. The amount of shrinkage for a shrinkage of 20% by volume when using theobromine as the shaping material is then selected to be 42 micrometers and the laminar structure is sintered at at least 1000 degrees Celsius. $ZrO_2$ with four mol-percent of $Y_2O_3$ was selected as the ceramic material.

The electrodes 28/29 for the cathode and/or the corresponding anode of the sensor preferably consist of a metal from the platinum group, in particular platinum, or of alloys of the platinum group or alloys of the metals of the platinum group with other materials, such as described, among others, in DE PS 41 00 106. If necessary, they are supplied with a support frame material of zirconium oxide, which has been ceramically stabilized with yttrium, for example, in the form of a YSZ powder of a volume proportion of preferably approximately 40 percent by volume. They are porous and as thin as possible. They preferably have a thickness of 8 to 15 micrometers. The strip conductors associated with the electrodes are preferably also made of platinum or a platinum alloy of the type described. Furthermore, they can also be produced on the basis of a paste on a noble metal-cermet base.

The solid electrode layer (intermediate layer) 14 or 32 consists of one of the known oxides used for producing bivalently negative solid electrolyte foils which conduct oxygen ions, such as in particular $ZrO_2$, $CeO_2$, $HfO_2$ and $ThO_2$, for example, with a content of bivalent earth alkali oxides and/or trivalent oxides of rare earths. In a typical manner the layer can consist of approximately 80 to 90 mol percent of $ZrO_2$, $CeO_2$, $HfO_2$ or $ThO_2$ and 3 to 20 mol percent of MgO, CaO, SrO and/or oxides of the rare earths and/or particularly $Y_2O_3$. In an advantageous manner the layer consists of $ZrO_2$, stabilized with $Y_2O_3$. $Sc_2O_3$ can be used as a complete or partial replacement for $Y_2O_3$. In an advantageous manner the thickness of the layer can be around 10 to 22 micrometers, in particular 15 to 50 micrometers.

The diffusion conduit can have a filler of a rough, porously sintering material, for example, on a basis of $Al_2O_3$ or $ZrO_2$.

Thermal carbon black powder, graphite, plastics, for example on the basis of polyurethane, salts, for example ammonium carbonate, and other organic substances, such as theobromine and indanthrene blue, were employed as pore-forming means or shaping means for the shape of the gas measuring chamber 18 and/or the diffusion conduit 12 and/or the electrode chamber 25.

The selection of the chamber shapes is considerably widened. Self-contained structures also change their shape at sintering temperatures located above a threshold temperature of approximately 300 degrees Celsius which, for example, with the employment of theobromine, results in deformations of the structure because theobromine had already been completely removed from the hollow chamber structure. Stabilization, i.e., a structure true to shape, is only obtained at temperatures of more than approximately 700 degrees Celsius. Further advantages ensue when different shaping means are employed together by producing the volumes of individual hollow chambers, which are burned out, by combining, for example, gluing together, individual shaping partial volumes. Spacer elements can also be made of glass-ceramic materials. Example 7 was produced with the use of picein.

What is claimed is:

1. A sensor element for determining concentration of at least one constituent of a gas mixture and which operates on an electro-chemical measuring process, the sensor element comprising:

a gas measuring chamber;

a pair of electrodes and an electrode chamber located between the pair of electrodes; and a diffusion conduit adjoining the electrode chamber and having a gas input which connects with the gas measuring chamber, having a gas output which connects with the electrode chamber, and having at least one cross-sectional area including a height, w, and a length, L, which height, w, has a preselected minimum value, and which length, L, has a value which is equal to or greater than the preselected minimum value of the height, w, wherein the at least one constituent of the gas mixture has a mean free path length through the sensor element, wherein the gas measuring chamber has a cross-sectional area including a height and a length each of which are at least as large as the minimum height, w, of the diffusion conduit, and wherein the height, w, of respective ones of the at least one cross-sectional area of the diffusion conduit is at least a multiple of the mean free path length of the constituent of the gas mixture to be measured.

2. The sensor element in accordance with claim 1, further comprising a plurality of diffusion conduits and at least two cells selected from the group consisting of a short-circuit cell, a pumping cell, and a measuring cell, which at least two cells are connected with the gas measuring chamber by respective diffusion conduits.

3. The sensor element in accordance with claim 1, wherein the mean free path length has a minimum value for the gas constituent to be measured, and wherein the diffusion conduit has a ratio of height-to-length, w:L, ranging from 2 to 4:70 to 90 while the preselected minimum value of the mean free path length is maintained.

4. The sensor element in accordance with claim 1, wherein the gas constituent to be measured has a mean free path length, and wherein at least one of the height and length of respective ones of the at least one cross-sectional area of the diffusion conduit is at least a multiple of ten times the mean free path length of the gas constituent to be measured.

5. The sensor element in accordance with claim 4, wherein at least one of the height and length of respective ones of the at least one cross-sectional area of the diffusion conduit is at least a multiple of one hundred times the mean free path length of the gas constituent to be measured.

6. The sensor element in accordance with claim 1, wherein the diffusion conduit has a plurality of gas inputs from the gas measuring chamber and a plurality of gas outputs.

7. The sensor element in accordance with claim 1, wherein the mean free path length has a minimum value for the constituent of the gas mixture to be measured, wherein the height, w, of respective ones of the at least one cross-sectional area of the diffusion conduit has a fixed minimum value (w) which is expressed as a multiple of the minimum value of the mean free path length of the constituent of the gas mixture to be measured, and wherein the gas measuring chamber and the diffusion conduit each have an arbitrary structural shape.

8. The sensor element in accordance with claim 1, further comprising at least one gas measuring chamber for reference gas, wherein the preselected minimum value of the height, w, is preselected so that substantially only gaseous phase diffusion occurs whereby the sensor element is substantially non-pressure-sensitive.

9. The sensor element according to claim 8, wherein the gas constituent to be measured is selected from the group consisting of air, pure oxygen, and pure nitrogen, wherein the mean free path length for the gas constituent at a sensor operation temperature of 20° C. and at a sensor operation temperature of 1 bar is 0.08 micrometers, and wherein the minimum height, w, of respective ones of the at least one cross-sectional area of the diffusion conduit is at least a multiple of 100 of the mean free path length of the oxygen anion to be measured and is at least 8 micrometers.

10. The sensor element according to claim 9, wherein the gas constituent to be measured is oxygen, wherein the mean free path length for an oxygen anion at a sensor operation temperature of 800° C. and at a sensor operation temperature of 1 bar is 0.3 micrometers, and wherein the minimum height, w, of respective ones of the at least one cross-sectional area of the diffusion conduit is at least a multiple of 100 of the mean free path length of the oxygen anion to be measured and is at least 30 micrometers.

11. The sensor element in accordance with claim 10, wherein the gas measuring chamber, the diffusion conduit, and the electrode chamber have respective shapes provided by application of respective shaping means and are joined by adhesive means.

12. The sensor element in accordance with claim 1, wherein the diffusion conduit has at least one gas output to the electrode chamber, and wherein the diffusion conduit widens into a funnel-shaped extension at at least one of the at least one gas output.

13. The sensor element in accordance with claim 1, wherein the gas measuring chamber, the diffusion conduit, and the electrode chamber have respective shapes which are provided by a silk screening process and by application of shaping means.

14. The sensor element in accordance with claim 1, further comprising a measuring cell adjoining the diffusion conduit and having first and second electrodes, and an intermediate layer provided between the first and second electrodes, the first electrode connecting with the gas output of the diffusion conduit, wherein the first and second electrodes have a shape which is one of an annular ring or a sector of a circle.

15. The sensor element according to claim 1, wherein the gas mixture to be measured includes at least one constituent or at least one constituent which is chemically related to the at least one constituent, and wherein the sensor element is an exhaust gas probe for determining the concentration of at least one constituent of a gas mixture of an internal combustion engine.

16. The sensor element according to claim 1, wherein the at least one constituent of the gas mixture has a mean free path length through the sensor element which is characteristic of the repsective constituent of the at least one constituent and which has a minimum value, and wherein the predetermined minimum value of the height, w, of the diffusion conduit is at least a multiple of the minimum value of the mean free path length of the constituent of the gas mixture to be measured so that substantially only gaseous phase diffusion occurs.

* * * * *